US00PP30020P2

(12) United States Plant Patent
Wood

(10) Patent No.: US PP30,020 P2
(45) Date of Patent: Dec. 25, 2018

(54) ***HYDRANGEA* PLANT NAMED 'SMHSMAKF2'**

(50) Latin Name: *Hydrangea paniculata*
Varietal Denomination: SMHSMAKF2

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/731,372

(22) Filed: Jun. 2, 2017

(51) Int. Cl.
*A01H 5/00* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Cassandra Bright

(57) ABSTRACT

A new and distinct *Hydrangea* cultivar named 'SMHSMAKF2' is disclosed, characterized by a large lace cap inflorescence. Plants are compact, re-bloom and have a distinctive hardiness, with frost resistant flower buds. The new variety is a *Hydrangea*, normally produced as an ornamental plant for containers or gardens.

2 Drawing Sheets

Figure 1:
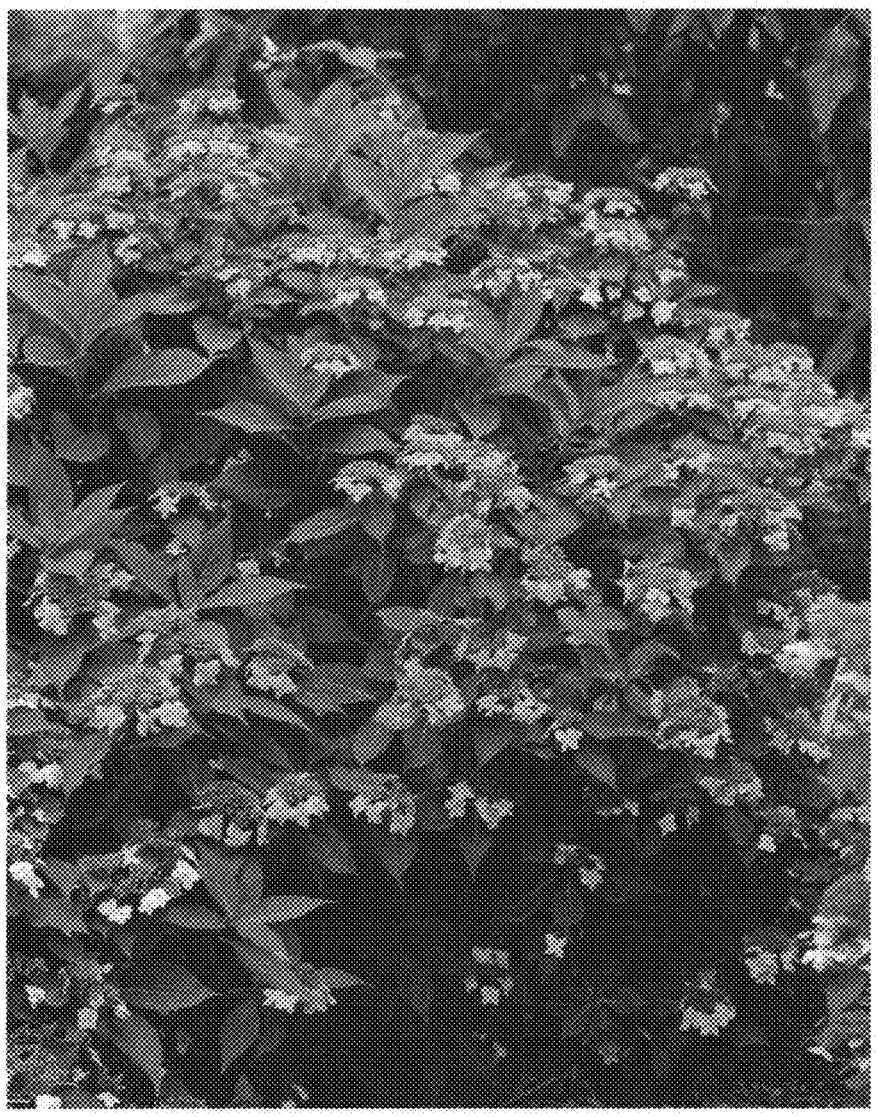

Latin name of the genus and species: *Hydrangea paniculata.*

Variety denomination: 'SMHSMAKF2'.

BACKGROUND OF THE INVENTION

The new *Hydrangea* cultivar is a product of a planned breeding program conducted by the inventor, Timothy Wood, in Grand Haven, Mich. The objective of the breeding program was to produce new *Hydrangea* varieties for garden use. The open pollination resulting in this new variety was made during 2004.

The seed parent is the unpatented commercial variety *Hydrangea paniculata* 'Maiko'. The pollen parent is unknown, as it was an open pollination breeding program. The new variety was identified as a potentially interesting selection June of 2007, at a greenhouse in Grand Haven, Mich.

Asexual reproduction of the new cultivar 'SMHSMAKF2' by softwood cuttings was first performed in July of 2007, at commercial greenhouse in Grand Haven, Mich. Subsequent propagation has shown that the unique features of this cultivar are stable and reproduced true to type in multiple successive generations.

SUMMARY OF THE INVENTION

The cultivar 'SMHSMAKF2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMHSMAKF2' These characteristics in combination distinguish 'SMHSMAKF2' as a new and distinct *Hydrangea* cultivar:

1. Large lace cap inflorescence.
2. Compact growth habit.

3. Hardy, frost resistant flower buds.
4. Re-blooming habit.

PARENT COMPARISON

Plants of the new cultivar 'SMHSMAKF2' are similar to plants of seed parent, in most horticultural characteristics, however, plants of the new cultivar 'SMHSMAKF2' differ in the following:

1. The new variety produces a larger inflorescence.
2. The new variety produces bright pink flower, the seed parent produces lighter colored lavender to pink flowers. Pollen parent unknown as this is product of open pollination.

COMMERCIAL COMPARISON

'SMHSMAKF2' can be compared to the patented commercial variety *Hydrangea paniculata* 'MAK20' U.S. Plant Pat. No. 24,820. These varieties are similar in most horticultural characteristics; however 'SMHSMAKF2' differs in the following:

1. The comparator has a smaller inflorescence.
2. Plants of the new variety are larger 'SMHSMAKF2' can be compared to the patented commercial variety *Hydrangea paniculata* 'SMNMAKTSR', U.S. Plant Pat. No. 28,672. These varieties are similar in most horticultural characteristics, however 'SMHSMAKF2' differs in the following:

1. The comparator has approximately double the amount of fertile and sterile flowers per inflorescence than 'SMHSMAKF2'.
2. The new variety has sepals colored Red-Purple 67C at maturity, comparator has sepals colored near 63A with the base colored near Yellow-Green 145C and 144D at maturity.
3. This comparator has foliage with a dark margin, flushed Greyed-Purple 187A, foliage of the new variety does not have this dark flush.

'SMHSMAKF2' can be compared to the patented commercial variety *Hydrangea paniculata* 'MAKD', U.S. Plant Pat. No. 24,842. These varieties are similar in most horticultural characteristics, however 'SMHSMAKF2' differs in the following:

1. The new variety has sepals colored Red-Purple 67C at maturity, this comparator has sepals colored near Violet-Blue 92A and 92B.
2. Plants of the new variety have a larger habit; this comparator is very compact.
3. The comparator has approximately double the amount of fertile flowers per inflorescence than 'SMHSMAKF2'.

New cultivar has more intense pink flowers; comparator has lighter pink flowers.

BRIEF DESCRIPTION OF THE PHOTOGRAPHS

The accompanying photograph in FIG. 1 illustrates in full color a typical plant of 'SMHSMAKF2" grown in a field, in Grand Haven, Mich., USA. Age of the plant photographed is approximately 3 years.

Figure 2:
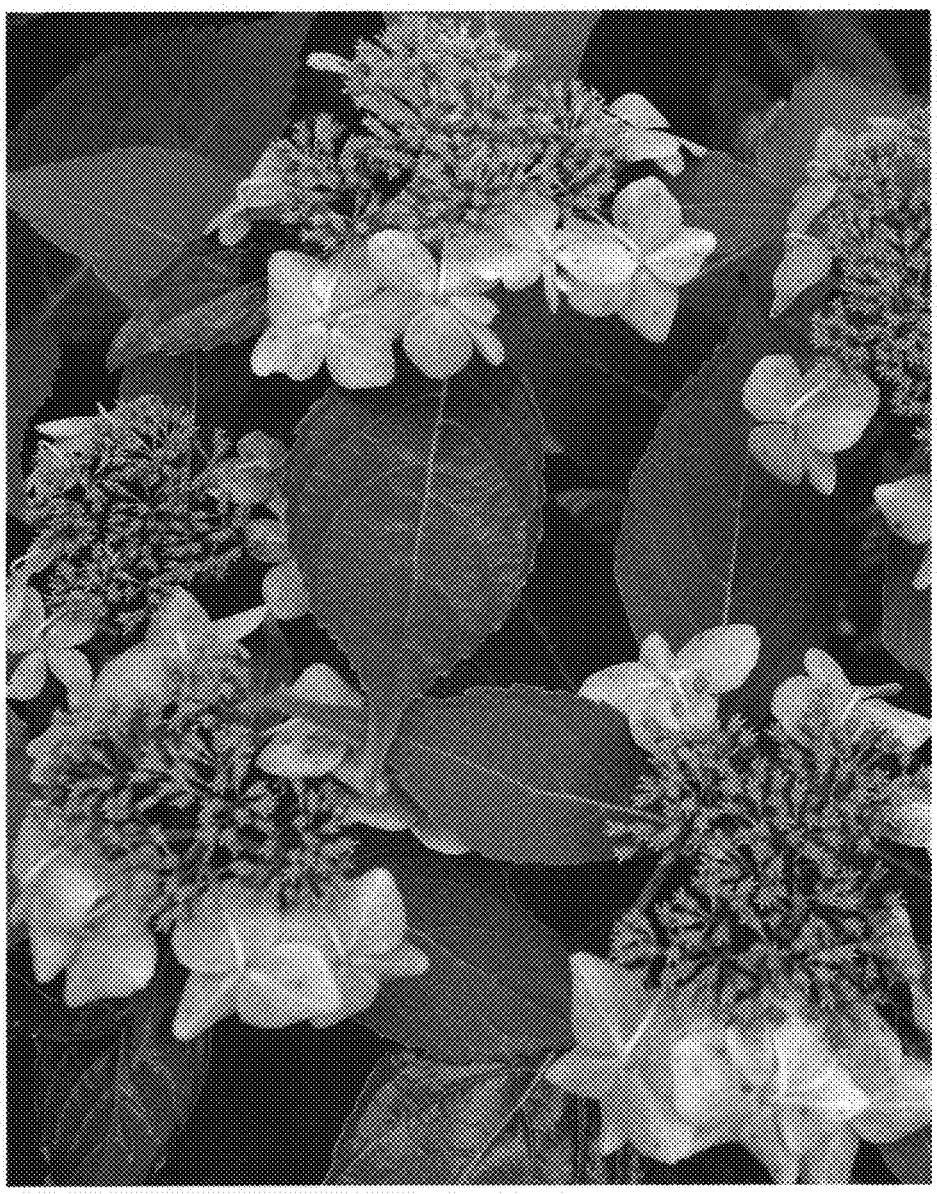

FIG. 2 illustrates typical foliage and inflorescence of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The 2015 Royal Horticultural Society Colour Chart except where general terms of ordinary dictionary significance are used. The following observations and measurements describe 'SMHSMAKF2' plants grown in a field, in Grand Haven, Mich., USA. The growing temperature ranged from approximately 18° C. to 27° C. daytime and 5° to 10° C. at night. Measurements and numerical values represent averages of typical plant types. Measurements were taken during May of 2016.

Botanical classification: *Hydrangea paniculata* 'SMHSMAKF2.'

PROPAGATION

Time to initiate roots: Approximately 18 days at approximately 24° C.

Time to produce a rooted young plants: Approximately 60 days at approximately 24° C.

Root description: Thin to thick, moderate to dense, freely root branching, fleshy. Color is white and brown.

Propagation method: Softwood cuttings.

PLANT

Age of plant described: 1 to 2 years.

Pot size: 1 gallon.

Growth habit: Flowering perennial shrub, or sub-shrub.

Overall plant shape: Mounded.

Height: 35 cm.

Plant spread: 43 cm.

Growth rate: Moderate.

Plant vigor: Good.

Branching characteristics: Upright/outward basal branches, some pinching required.

Length of lateral branches: 19.2 cm.

Number of lateral branches: 11.

Diameter of lateral branches: 4.5 mm.

Lateral branch shape: Rounded.

Lateral branch strength: Good.

Internode length: Average 6.7 cm.

Branch color: Immature: Near RHS Yellow-Green 146C. Mature: Near RHS Yellow-Green 146C.

Branch aspect: 10-45°.

Branch texture: Pubescent with moderate quantity of lenticels. Lenticels 2 to 4 mm, colored near Greyed-Purple 187B.

FOLIAGE

Leaf:

*Arrangement.*—Opposite.

*Average length.*—12.3 cm.

*Average width.*—7.1 cm.

*Shape of blade.*—Elliptic.

*Apex.*—Acuminate.

*Base.*—Obtuse.

*Margin.*—Serrate to crenate.

*Texture and appearance of top surface.*—Rugose, leathery.

*Texture and appearance of bottom surface.*—Leathery, prominent veins.

*Leaf pubescence.*—Occurs on upper and lower surfaces, sparse along veins.

*Color.*—Young foliage upper side: Near RHS Green 135A. Young foliage under side: Near RHS Green 137C. Mature foliage upper side: Near RHS Green 131A. Mature foliage under side: Near RHS Green 137D.

*Venation.*—Type: Pinnate-arculate. Venation color upper side: Near RHS Green 138B. Venation color under side: Near Yellow-Green 1444B.

Petiole:

*Average length.*—1.6 cm.

*Diameter.*—3.5 mm.

*Color.*—Upper side: Near RHS Yellow-green 144A. Under side: Near RHS Yellow-green 144A.

*Texture upper side.*—Smooth.

*Texture under side.*—Smooth.

FLOWER

Bloom period:

*Natural season.*—Mid-Summer through Fall.

Inflorescence:

*Type.*—Lacecap.

*Quantity of flowers per inflorescence.*—Fertile flowers: Average 79. Sterile Flowers: Average 7.

*Persistent or self-cleaning.*—Persistent.

*Fragrance.*—Mild and slightly sweet.

Panicle:

*Shape.*—Flattened half sphere.

*Height.*—6.5 cm.

*Diameter.*—13.5 cm.

Sterile flower:

*Bud shape.*—Elongated orbicular.

*Bud length.*—Average 12 mm.

*Bud diameter.*—Average 9 mm.

*Bud color.*—Near RHS Green 142D.

*Flower aspect.*—Outward.

*Flower shape.*—Irregularly round.

*Flower length.*—Average 6.9 cm.

*Flower diameter.*—Average 6.9 cm.

*Flower depth.*—0.9 cm.

Sterile flower petals:
*Petal arrangement*.—Whorled.
*Length of petal*.—3.2 mm.
*Width of petal*.—2.8 mm.
*Apex*.—Acute.
*Shape of petal*.—Ovate.
*Petal margin*.—Entire.
*Petal base*.—Obtuse.
*Petal number*.—4 to 5.
*Petal texture*.—Smooth, glabrous, upper and under side.
*Color*.—Upper surface at first opening: Near RHS Yellow-Green 151D flushed Red-Purple 63D. Upper surface at maturity: Near RHS Yellow-Green 151D flushed Red-Purple 63D. Under surface at first opening: Near RHS Yellow-Green 151D flushed Red-Purple 63D. Under surface at maturity: Near RHS Yellow-Green 151D flushed Red-Purple 63D. Upper surface fading to: Near RHS Yellow-Green 151D flushed Red-Purple 63D. Lower surface fading to: Near RHS Yellow-Green 151D flushed Red-Purple 63D.

Sterile flower sepal:
*Arrangement*.—Whorled, double whorled.
*Number*.—5 to 10.
*Shape*.—Wide deltate.
*Tip*.—Acute.
*Base*.—Truncate.
*Margin*.—Irregularly dentate and undulate.
*Length*.—Outer whorl 3.6 cm, inner whorl 2.5 cm.
*Width*.—Outer whorl 3.6 cm, inner whorl 2.2 cm.
*Texture, upper*.—Smooth, glabrous.
*Texture, lower*.—Smooth, glabrous.
*Color*.—Upper surface at first opening: Near RHS Green 142D. Upper surface at maturity: Near RHS Red-Purple 67C. Under surface at first opening: Near RHS Green 142D. Under surface at maturity: Near RHS Red-Purple 65B. Upper surface fading to: Near RHS Red-Purple 65B. Lower surface fading to: Near RHS Red-Purple 65C.

Sterile flower pedicel:
*Angle*.—About 70° from attachment.
*Strength*.—Moderately strong.
*Length*.—2.7 cm.
*Width*.—2 mm.
*Texture*.—Irregularly verrucate.
*Color*.—Near RHS Red-Purple 65A.

Fertile flower:
*Bud shape*.—Orbicular and lobed.
*Bud length*.—4.5 mm.
*Bud diameter*.—5.8 mm.
*Bud color*.—Near RHS Green 142D flushed Red-Purple 67D.
*Flower aspect*.—Upright and outwardly facing.
*Flower shape*.—Round, somewhat star-shaped.
*Flower length*.—1.0 cm.
*Flower diameter*.—1.0 cm.
*Flower depth*.—8 mm.
*Persistence*.—Self-cleaning.

Fertile flower petals:
*Length of petal*.—5.0 mm.
*Width of petal*.—2.5 mm.
*Apex*.—Acute.
*Shape of petal*.—Ovate.
*Petal margin*.—Entire.
*Petal arrangement*.—Whorl.
*Petal number*.—6.
*Petal base*.—Truncate.
*Petal texture*.—Smooth, glabrous, upper and under side.
*Color*.—Upper surface at first opening: Ranging from Red-Purple 65D, through 65A, colors present together as a spectrum over petal. Upper surface at maturity: Near Red-Purple 73A. Under surface at first opening: Ranging from Red-Purple 65D, through 65A, overlaying Greyed-Green 195D. Under surface at maturity: Near Red-Purple 73D. Upper surface fading to: Near RHS Near Red-Purple 73A. Lower surface fading to: Near Red-Purple 73D.

Fertile flower sepal:
*Arrangement*.—Whorled.
*Number*.—5 to 7.
*Shape*.—Wide deltate.
*Tip*.—Acute.
*Base*.—Truncate.
*Margin*.—Entire.
*Length*.—1 mm.
*Width*.—0.75 mm.
*Texture, upper*.—Smooth, glabrous.
*Texture, lower*.—Smooth, glabrous.
*Color*.—Upper surface at first opening: Near RHS Yellow-Green 149D. Upper surface at maturity: Near RHS Yellow-Green 149D. Under surface at first opening: Near RHS Yellow-Green 149D. Under surface at maturity: Near RHS Red-Purple 65B. Upper surface fading to: Near RHS Yellow-Green 149D. Lower surface fading to: Near RHS Yellow-Green 149D.

Fertile flower pedicel:
*Angle*.—Range of 40-80° from attachment.
*Strength*.—Moderate.
*Length*.—4.1 mm.
*Width*.—0.5 mm.
*Texture*.—Smooth.
*Color*.—Near RHS Yellow-green 149D flushed Greyed-Purple 187C.

REPRODUCTIVE ORGANS

Sterile flower:
*Stamen number*.—8.
*Filament length*.—1.5 mm.
*Filament color*.—Near RHS Green 138D.
*Anther shape*.—Obcordate, lopsided apex.
*Anther color*.—Near RHS Yellow-Green 149B.
*Anther length*.—1.5 mm.
*Pollen amount*.—Not present.
*Gynoecium*.—Yes.
*Pistil number*.—4.
*Pistil length*.—2 mm.
*Stigma shape*.—Capitate.
*Style length*.—1.5 mm.
*Style color*.—Near RHS Greyed-Green 196D.
*Ovary color*.—Near RHS Yellow-Green 144B.

Fertile flower:
*Stamen number*.—14 to 17.
*Filament length*.—4.5 mm.
*Filament color*.—Near RHS Red-Purple 65B.
*Anther shape*.—Liner.
*Anther length*.—0.75 mm.

*Anther color*.—Near RHS Greyed-Purple N187C.
*Pollen amount*.—Moderate.
*Pollen color*.—Near RHS White 155B.
*Pistil number*.—7 to 10.
*Pistil length*.—1.6 mm.
*Stigma shape*.—Capitate.
*Stigma color*.—Near RHS White N155C.
*Style length*.—1.0 mm.
*Style color*.—Near RHS Red-Purple 65B.
*Ovary color*.—Near RHS Red-Purple 65B.

OTHER CHARACTERISTICS

Disease resistance: Neither resistance nor susceptibility to diseases or pests has been observed in this variety.
Cold tolerance: −32° C. to 36° C.
Fruit/seed production: Not observed.

What is claimed is:

1. A new and distinct cultivar of *Hydrangea* plant named 'SMHSMAKF2' as herein illustrated and described.

* * * * *